United States Patent
Lloyd et al.

(10) Patent No.: US 9,956,272 B2
(45) Date of Patent: May 1, 2018

(54) METHODS FOR PREPARING FACTOR X, ACTIVATED FACTOR X, INACTIVATED FACTOR X AND INACTIVATED FACTOR XA, AND PHARMACEUTICAL COMPOSITIONS COMPRISING SAME

(75) Inventors: Joanne Lloyd, Hertfordshire (GB); Peter Feldman, Hertfordshire (GB)

(73) Assignee: Bio Products Laboratory Limited, Hertfordshire (GB)

( * ) Notice: Subject to any disclaimer, the term of this patent is extended or adjusted under 35 U.S.C. 154(b) by 507 days.

(21) Appl. No.: 14/051,094

(22) PCT Filed: May 29, 2008

(86) PCT No.: PCT/GB2008/001810
§ 371 (c)(1),
(2), (4) Date: Apr. 11, 2014

(87) PCT Pub. No.: WO2008/145989
PCT Pub. Date: Dec. 4, 2008

(65) Prior Publication Data
US 2014/0322194 A1    Oct. 30, 2014

Related U.S. Application Data

(62) Division of application No. 12/601,930, filed as application No. PCT/GB2008/001810 on May 29, 2008, now Pat. No. 8,906,366.

(30) Foreign Application Priority Data

May 30, 2007 (GB) .................................. 0710321.1

(51) Int. Cl.
*A61K 38/48* (2006.01)
*C12N 9/64* (2006.01)

(52) U.S. Cl.
CPC ........ *A61K 38/4846* (2013.01); *C12N 9/6432* (2013.01)

(58) Field of Classification Search
CPC ..................... A61K 38/4846; C12N 9/6432
See application file for complete search history.

(56) References Cited

U.S. PATENT DOCUMENTS

| | | | |
|---|---|---|---|
| 4,481,189 A | 11/1984 | Prince | |
| 4,501,731 A * | 2/1985 | Tishkoff | C12N 9/6432 424/530 |
| 4,540,573 A | 9/1985 | Neurath et al. | |
| 4,613,501 A | 9/1986 | Horowitz | |
| 5,589,571 A | 12/1996 | King | |
| 5,593,968 A * | 1/1997 | Turecek | C12N 9/6432 435/68.1 |
| 6,573,071 B1 | 6/2003 | Himmelspach et al. | |
| 2003/0180287 A1 | 9/2003 | Gombotz et al. | |

FOREIGN PATENT DOCUMENTS

| | | | |
|---|---|---|---|
| EP | 0617049 A1 | 9/1994 | |
| WO | 8905650 A2 | 6/1989 | |
| WO | 9015619 A1 | 12/1990 | |
| WO | 9401466 A1 | 1/1994 | |
| WO | 9613274 A1 | 5/1996 | |
| WO | 0151067 A1 | 7/2001 | |
| WO | 04050904 A1 | 6/2004 | |
| WO | WO 2005117912 A1 * | 12/2005 | ........... A61K 31/727 |
| WO | 06067230 A1 | 6/2006 | |

OTHER PUBLICATIONS

Baker et al. Warfarin reversal: consensus guidelines, on behalf of the Australasian Society of Thrombosis and Haemostasis. MJA. vol. 181, No. 9, 2004. p. 492-497.*
Wolf et al. Procoagulant Activity of Reversibly Acylated Human Factor Xa. Blood, vol. 86, No. 11 (Dec. 1), 1995: pp. 4153-4157.*
Venkateswarlu et al. Structure and Dynamics of Zymogen Human Blood Coagulation Factor X. Biophysical Journal vol. 82 Mar. 2002 1190-1206.*
Husi, et al., "Purification of Factor X by Hydrophobic Interaction Chromatography," Journal of Chromatography B, Jan. 31, 2001, 6 pages.
Husi, et al, "Separation of Human Vitamin K-dependent coagulation proteins using hydrophobic interaction chromatography," Journal of Chromatography B, Sep. 17, 1999, 13 pages.
Feldman, P.A. et al., "Large scale preparation and biochemical characterization of a new high purity factor IX concentrate prepared by metal chelate affinity chromatography," Blood Coagulation & Fibrinolysis: An International Journal in Haemostasis and Thrombosis 5:939-948 (Dec. 1994).
International Search Report and Written Opinion from PCT/GB2008/001810, dated Oct. 27, 2008.
Feldman, P.A. et al., "Preparation of a high purity factor IX concentrate using metal chelate affinity chromatography," Biotechnology of Blood Proteins 227:63-68 (Jan. 1, 1993).
Kaiser, B. et al., "Inactivation of factor Xa by the synthetic inhibitor DX-9065a causes strong anticoagulant and antiplatelet actions in human blood," Blood Coagulation & Fibrinolysis 10(8):495-501 (Dec. 1999).
International Preliminary Report on Patentability from PCT/GB2008/001810, dated Jun. 29, 2009.

* cited by examiner

*Primary Examiner* — Taeyoon Kim
(74) *Attorney, Agent, or Firm* — Armstrong Teasdale LLP

(57) ABSTRACT

Methods for preparing Factor X, activated Factor X, inactivated factor X and inactivated factor Xa, compositions comprising Factor X and Factor Xa, inactivated Factor X and inactivated Factor Xa and methods of medical treatment using Factor X, Factor Xa, activated Factor X and inactivated Factor Xa are disclosed. The preparation methods comprise a chromatography step using an immobilised metal ion affinity chromatography substrate.

4 Claims, 2 Drawing Sheets

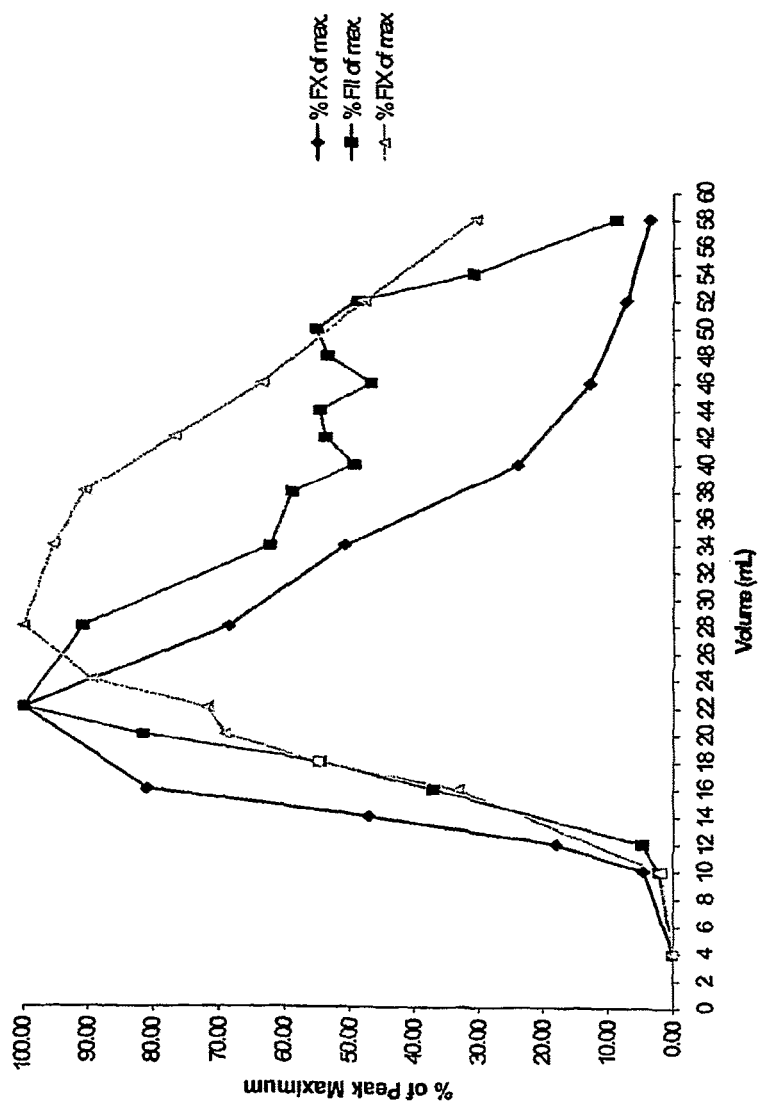
Figure 1. Elution profile for factors X, II and IX during anion exchange chromatography.

Figure 2. Flow Chart of Preferred Process
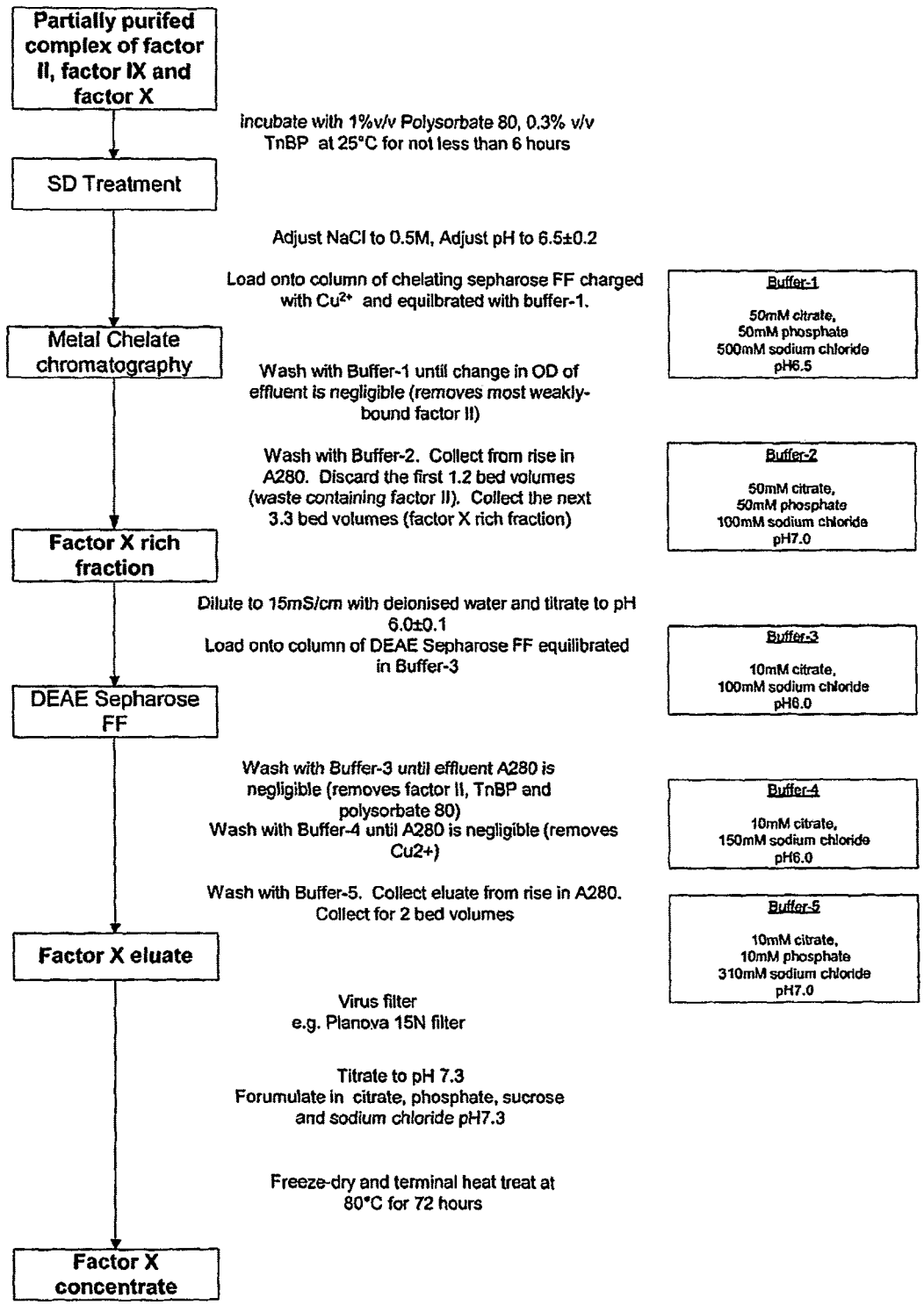

METHODS FOR PREPARING FACTOR X, ACTIVATED FACTOR X, INACTIVATED FACTOR X AND INACTIVATED FACTOR Xa, AND PHARMACEUTICAL COMPOSITIONS COMPRISING SAME

CROSS REFERENCE TO RELATED APPLICATIONS

This application is a divisional application of U.S. application Ser. No. 12/601,930, filed on Nov. 25, 2009, which is a U.S. National Phase patent application of International Application Serial Number PCT/GB2008/001810, filed on May 29, 2008, which is herein incorporated by reference in its entirety, and which claims priority from Great Britain Patent Application 0710321.1, filed on May 30, 2007, which is herein incorporated by reference in its entirety.

BACKGROUND OF THE INVENTION

The present invention relates to methods for preparing factor X, activated factor X (factor Xa), inactivated factor X and inactivated factor Xa, compositions comprising factor X, factor Xa, inactivated factor X or inactivated factor Xa which are suitable for pharmaceutical use, and use of factor X, factor Xa, inactivated factor X or inactivated factor Xa for the treatment of various medical conditions.

Factor X is a coagulation factor normally present in human blood. Factor X deficiency is a rare bleeding disorder which affects between 1 in 500,000 and 1 in 1,000,000 of the population. It is characterised by a tendency to excessive bleeding, similar to that caused by factor VIII and factor IX deficiencies in haemophilia A and B respectively. There are currently no licensed treatments specifically for factor X deficiency anywhere in the world. In particular, there are no clinical concentrates of factor X currently available for use in the treatment of factor X deficiency. Instead, physicians have to rely on infusions of plasma or of prothrombin complex concentrates (PCC). However, there are a number of disadvantages accompanying use of plasma or PCC for the treatment of factor X deficiency.

Plasma contains only a low concentration of factor X (approximately 1 unit per mL), so a very large infusion volume is needed to achieve even a small increase in a patient's circulating level of factor X. Treatment is constrained by the need to stop infusion before a fully-therapeutic dose has been delivered, to avoid volume overload causing osmotic imbalance and transfusion-related acute lung injury. Plasma also requires refrigerated or frozen storage which can restrict availability to the patient.

Prothrombin complex concentrates (PCC) contain some factor X, but this is only a very minor component of the total protein present. PCCs are not assayed or labelled for this indication which leads to highly variable dosing. Many of these older products are made from pooled plasma without the added safety margin of multiple virus inactivation steps during manufacture. Most require refrigerated storage which, like plasma, can restrict availability to the patient. As the main constituent of PCC is prothrombin, and PCCs carry a risk of being partially activated by the manufacturing process, there is a risk that use of PCC will result in a thrombotic side effect during treatment, which could be fatal. Although PCC contain more factor X than plasma in the available volume, it is desirable to contain the therapeutic dose in as small a volume as possible, particularly as many of the treated patients are young children.

WO 89/05650 discloses a method for at least partially separating vitamin K-dependent blood clotting factors, including Factor X, from a mixture containing at least one such factor, for example a prothrombin complex concentrate. The method comprises adsorption of the mixture onto a metal chelate chromatography column. However, factor X produced according to the method in WO 89/05650 still contains significant amounts of prothrombin, up to 40-50% by weight. The presence of prothrombin in a concentrate of factor X is undesirable because prothrombin has a longer circulating half-life than factor X. If a patient is infused with treatment containing both proteins, this can cause a disproportionate and cumulative increase in plasma prothrombin which may then unbalance the haemostatic equilibrium in favour of thrombin generation and clot formation (haemostasis/thrombosis). Removal or reduction of prothrombin in a factor X concentrate would be desirable to minimise the risk of spontaneous thrombin generation during the manufacture or storage of the product, which could cause also thrombotic reactions during clinical use.

There is therefore still a need for a process for the preparation of factor X which is efficient, can be carried out on an industrial scale, which allows incorporation of multiple virus reduction steps and which provides a pharmaceutically useful product. There is also a need for pharmaceutical formulations of factor X for use in the treatment of conditions such as factor X deficiency.

SUMMARY

In one aspect, the invention therefore provides a method for the separation of factor X from a starting material comprising factor X and prothrombin, the method comprising use of immobilised metal ion affinity chromatography (IMAC, also referred to as metal chelate chromatography). The method comprises:
a) adsorbing the starting material onto an immobilised metal ion affinity chromatography substrate;
b) eluting selected adsorbed proteins from the substrate; and
c) monitoring the eluate for commencement of elution of prothrombin and factor X, discarding a first portion of the eluate and collecting a subsequent second portion of the eluate enriched in factor X.

Preferably, the factor X is human factor X. Also preferably, the factor X obtained in step c) is further purified by anion exchange chromatography. Anion exchange chromatography can provide additional separation of factor X from prothrombin. In addition, it provides a gentle method for concentrating the factor X to a pharmaceutically-useful potency for formulation. Alternatively, the factor X could be concentrated after step c) using a process such as ultrafiltration. However, this may lead to greater mechanical loss and physical damage to the factor X than does anion exchange chromatography.

BRIEF DESCRIPTION OF THE DRAWINGS

FIG. 1 illustrates an elution profile for factors X, II, and IX during anion exchange chromatography according to one aspect of the present disclosure.

FIG. 2 illustrates a flowchart of an example process according to the present disclosure.

DETAILED DESCRIPTION

In the method disclosed in WO 89/05650, the prothrombin and the factor X co-elute from the substrate, leading to factor X fractions which contain high amounts of prothrombin. Surprisingly, it has now been found that prothrombin is eluted preferentially at the front of the protein elution peak, whilst the factor X is eluted at a substantially constant concentration throughout the protein elution. It is therefore possible to exclude the main peak of protein elution, and collect factor X only in the tail part of the peak without significant loss of yield and with considerable increase in purity compared to the method disclosed in WO 89/05650.

The starting material for the method of the invention may be any solution comprising at least prothrombin and factor X. Preferably, the starting material will be plasma or a plasma-derived fraction such as cryoprecipitate-depleted plasma and/or Fraction I-depleted plasma, more preferably an extract from a plasma fraction. Most preferably, the starting material is a mixture of prothrombin (factor II), factor IX and factor X, for example prothrombin complex. Other proteins including factor VII, protein C, protein S, protein Z and inter-alpha-trypsin inhibitor may also be present. Also preferably, the factor X will be human factor X. Alternatively, the starting material could be a solution collected from a transgenic tissue or even from recombinant culture medium from which a contaminating and co-fractionating protein such as prothrombin is also harvested.

The starting material may be prepared by any suitable method known in the art. For example, methods for the separation of prothrombin complex from plasma and plasma fractions are well known in the plasma fractionation industry. Prothrombin complex is most commonly isolated from plasma and plasma fractions (e.g. cryoprecipitate-depleted plasma, fraction I precipitate-depleted plasma or a mixture of cryoprecipitate and fraction I precipitate-depleted plasma) by anion-exchange chromatography. An alternative source of prothrombin complex-enriched starting material is the precipitate generated by ethanolic fractionation of plasma. In this process, different plasma proteins are partitioned into different precipitate fractions by adjustment of ethanol concentration, temperature and pH. A particularly preferred starting material is prothrombin complex obtained from cryoprecipitate-depleted human plasma by anion exchange chromatography using an anion exchange medium such as DEAE-Sepharose (Feldman P A, Bradbury P I, Williams J D, Sims G E, McPhee J W, Pinnell M A, Harris L, Crombie G I, Evans D R, Large scale preparation and biochemical characterization of a new high purity factor IX concentrate prepared by metal chelate affinity chromatography, Blood Coagulation and Fibrinolysis 5: 939-948 (1994)). This anion exchange chromatography step can be performed chromatographically in column-mode, in bulk batch mode, or in a surface mode where the anion exchanger is attached to an inert filter or membrane support.

In step a) of the method of the invention, the starting material is loaded onto an IMAC substrate. Preferably, the substrate is present in a column for ease of processing. Any suitable metal ion may be used, including divalent metal ions such as copper, zinc or nickel, preferably copper. Suitable immobilised metal ion affinity chromatography substrates for use in the process of the invention include those disclosed in WO89/05650, methacrylate gel with multi-substituted ligands on the side chain spacers (e.g. Fractogel EMD Chelate from Merck), methacrylate gel with single chelating groups on the spacer arm (e.g. Toyopearl Chelate from Tosoh Bioscience), pressure-stable polymer with an iminodiacetic acid chelating functional group (e.g. Profinity IMAC from Bio-Rad Laboratories) and cross-linked agarose gel (e.g., chelating Sepharose FF from GE Healthcare). A preferred substrate is chelating Sepharose FF charged with copper ions.

Steps a) and b) of the method of the invention can be performed chromatographically in column-mode or in bulk batch mode. Alternatively, these steps may also be performed in a surface mode where the chelation complex is attached to an inert filter or membrane support. Column chromatography is however preferred for ease of operation on an industrial scale.

The loading conditions, including the buffer used, should be chosen such that the factor X (and co-binding prothrombin) in the starting material are bound to the substrate. The salt concentration of the starting material can be adjusted to minimize non-specific protein adsorption. Unwanted contaminants which do not bind or bind only weakly to the substrate may then be removed by washing. For example, if the starting material has previously been subjected to a solvent-detergent virus-inactivation step, most of the solvent or detergent reagents remaining do not bind to the substrate and are easily removed by washing. Any protein which is only weakly bound to the substrate may also be removed during the washing step. Alternatively, if the unwanted contaminants bind to the substrate they may be removed by selective elution before the factor X is eluted, or they may remain bound to the substrate whilst the factor X is selectively eluted.

Loading and washing can be performed at relatively high ionic strength (e.g. 500 mM sodium chloride and 100 mM buffer salts) to minimise non-specific binding of protein to the IMAC medium and to provide effective removal of most unwanted chemicals which may be present in the starting material. Inclusion of citrate in the buffer can remove some of the weakly-bound metal ions which may otherwise contaminate subsequently-eluted proteins.

The eluate should be monitored for protein content, for example by monitoring for absorbance at 280 nm. Absorbance at 280 nm is a measure of non-specific protein elution. Alternatively, the eluate could be sampled and assayed for prothrombin and factor X using methods known in the art. Initial washing should be continued until no more weakly bound protein is being eluted. Prothrombin and factor X may then be eluted using any suitable elution buffer. Elution of factor X may be achieved by reduction in the buffer ionic strength and/or change in the pH (e.g. from 6.5 to 7.0). Ionic strength reduction (e.g. from 500 mM NaCl to 100 mM NaCl) and an increase in the pH of the buffer (e.g. from 6.5 to 7.0) are preferred in order to differentiate between the factor X and other bound proteins.

Once protein elution is detected, the first portion of the eluate collected should be discarded, as it will contain high levels of prothrombin. Once the majority of the prothrombin has been eluted, a second portion of eluate enriched in factor X (compared to the starting material) should be collected. Once the elution behavior for a particular IMAC substrate/starting material/elution buffer is known, then it may be possible to identify the first and second portions of the eluate simply on the basis of eluate volume. For example, if the IMAC substrate is loaded into a column, then the first and second portions of the eluate may be defined by gel bed volume. In one non-limiting embodiment, the first portion of the eluate may comprise approximately the first 25% of the total eluate volume and the factor X-enriched second portion may comprise the subsequent approximately 75% of the total eluate volume. Alternatively, the prothrombin and factor X contents of different eluate fractions can be measured using methods known in the art. For example, the first portion could be collected until the ratio of prothrombin activity:factor X activity is less than about 0.01 unit/unit and the second, factor X-enriched portion after the ratio of prothrombin activity:factor X activity has fallen below about 0.01 unit/unit.

In a preferred embodiment, the second portion of the eluate enriched in factor X is further purified by anion exchange chromatography. It has surprisingly been found that anion exchange chromatography can be effective in removing residual prothrombin from the factor X, leading to an increase in purity of the factor X. It has been found that prothrombin binds slightly more strongly than factor X to anion exchange chromatography media, with the result that it is eluted slightly later than factor X. At the chosen ionic strength for elution, the prothrombin elution peak also tends to be broader than the factor X elution peak. The overall effect is that prothrombin elution can be delayed relative to factor X and the two can then be separated by selective collection of the eluate. The anion exchange chromatography step is also advantageous for removing any residual metal from the metal chelate substrate which may be present in the eluate, and/or any residual solvent detergent reagents which may be present. Careful selection of buffer chemistry during the anion exchange step allows for separation of factor X from contaminating prothrombin or factor IX (if present). The loading, washing and elution buffers for the anion exchange chromatography step should be chosen such that binding of the factor X to the media is maximised, and the separation of factor X from contaminating prothrombin is also maximised.

Any suitable anion exchange chromatography medium may be used. One particularly suitable medium is DEAE Sepharose anion exchange gel, for example DEAE Sepharose Fast Flow.

Preferably, the anion exchanger is equilibrated with buffers containing only citrate at about pH 6.0 before loading to maximise factor X binding. The loading conditions, including the buffer used, should be chosen such that factor X is bound to the medium. If necessary, the second portion of the eluate collected in step c) is diluted to reduce the ionic strength before loading onto the anion exchange chromatography medium. A suitable conductivity is 10-18 mS/cm. There is a maximum salt concentration/ionic strength beyond which factor X will not bind to the anion exchange chromatography medium. Preferably, the salt concentration is adjusted to provide maximum binding in the minimum volume, so as to avoid excessive column loading/adsorption times, which could compromise protein integrity or microbiological safety.

After loading, washing with a suitable buffer removes any unbound impurities, for example any residual solvent, detergent or metal which may be carried over from earlier processing steps. A preferred wash buffer contains both citrate and phosphate salts and raised sodium chloride concentration to remove any residual chemical reagents used during previous stages of purification. Use of such a wash buffer also removes citrate and phosphate anions which bind weakly to the anion exchange medium during equilibration and sample loading at low ionic strength, but does not elute factor X. It was found that removal of gel-bound citrate and phosphate ions at this stage prevented their release from the anion exchanger during the subsequent ionic strength step which eluted the bound protein. If not addressed by the wash buffer, it was found that the bound citrate and phosphate ions would be removed at the increased salt front produced by the subsequent elution buffer step, resulting in disruption of the salt (increased ionic strength) boundary and distortion of the sharp protein elution. This could potentially compromise both the factor X potency and its separation from other proteins.

Purified factor X is then eluted using a suitable elution buffer. Preferably, the constituents of the elution buffer are selected to elute factor X at a concentration which allows subsequent processing without the need for a separate concentration or diafiltration step. A preferred elution buffer contains approximately 10 mM citrate, 10 mM phosphate and 310 mM sodium chloride at pH7.0. This combination of salt and pH adjustment was found to elute factor X in a sharp peak, providing concentrated product which needed no further concentration before formulation to a pharmaceutical product.

After elution from the IMAC substrate, or from the anion exchange medium if used, the purified factor X may be formulated for pharmaceutical use. Preferably, this will involve freeze drying of the factor X, optionally in the presence of a suitable stabilizer, to give a factor X concentrate which is suitable for reconstitution for pharmaceutical use. A freeze dried factor X concentrate is preferred over a factor X solution as it will be stable for storage at higher temperatures and for longer periods than would a solution. It also provides a stable product which can be safely exposed to a terminal heat-treatment virus-inactivation step.

One advantage of the process of the invention is that it allows easy incorporation of one or more virus inactivation or reduction steps. Suitable virus inactivation or reduction methods are known in the art and include pasteurisation, solvent detergent treatment, dry heat treatment and virus filtration. Preferably at least two virus inactivation or reduction steps are included in the method, more preferably at least three.

For example, the starting material may be subjected to a virus inactivation step before it is loaded onto the immobilised metal ion affinity chromatography substrate. Solvent detergent virus inactivation may be carried out using reagents and methods known in the art (see for example U.S. Pat. Nos. 4,481,189, 4,613,501 and 4,540,573, all of which are hereby incorporated by reference). Suitable solvents include tri-n-butyl phosphate (TnBP) and ether, preferably TnBP. Suitable detergents include polysorbate (Tween) 80, polysorbate (Tween) 20, sodium cholate and Triton X-100.

A preferred detergent is polysorbate 80 and a particularly preferred solvent detergent combination is polysorbate 80 and TnBP.

A virus reduction step can be carried out on the eluate from either the metal chelate chromatography step or a subsequent anion exchange chromatography step. Filtration through a filter capable of removing viruses is preferred for the second virus reduction step. This includes commercially-available virus-retentive filters, for example the Planova 15N virus-retentive filter (available from Asahi Kasei Medical, Japan), the Ultipor DV20 filter (available from Pall Corporation), the Virosart CPV filter (available from Sartorius) and the Viresolve filters (available from Millipore). A preferred filter is the Planova 15N filter as it provides good protein flux and virus removal. Such filters also have the potential to reduce or remove prions or other causative agents of transmissible spongiform encephalopathy.

A virus inactivation step can also be carried out on the factor X after it has been formulated. For example, a freeze dried formulation can be subjected to a terminal dry heat treatment virus inactivation step. Such a step can involve heating the freeze dried formulation to about 80° C. for about 72 hours. These conditions are known to inactivate both enveloped and non-enveloped viruses.

In a preferred embodiment, the method of the invention comprises three virus reduction or inactivation steps: solvent detergent treatment of the starting material; virus filtration of the eluate from the metal chelate chromatography step or a subsequent anion exchange chromatography step; and dry heat treatment on the formulated final product.

In a most preferred embodiment, the method of the invention comprises:
i) solvent detergent treatment of a starting material comprising factor X and prothrombin;
ii) adsorbing the solvent detergent treated starting material onto an immobilized metal ion affinity chromatography substrate;
iii) eluting adsorbed proteins from the substrate;
iv) monitoring the eluate for commencement of elution of prothrombin/factor X, discarding a first portion of the eluate and collecting a subsequent second portion of the eluate enriched in factor X;
v) carrying out anion exchange chromatography to further purify the second portion of the eluate;
vi) filtering the product of step v) through a virus-retentive filter;
vii) freeze drying the filtered product of step vi), optionally in the presence of one or more stabilizers; and
viii) subjecting the freeze dried product to a virus reduction/inactivation heat treatment step.

FIG. 2 illustrates a most preferred embodiment of the method of the invention. The methods of the invention in one embodiment provide functional factor X which has not been adventitiously activated (i.e. "native" factor X). Activation is undesirable for the treatment of factor X deficiency because activated factor X may cause unwanted thrombogenic side-effects. However, in another embodiment, the methods of the invention may also be used to prepare activated factor X (factor Xa) by incorporating an activation step into the method. Factor X can be activated at any stage before formulation of the final product. The activation of factor X to factor Xa can be carried out at any stage during the methods of the invention, including:
on the starting material, for example the source plasma, a plasma fraction, or prothrombin complex;
on the factor X enriched eluate from the immobilised metal ion affinity chromatography step;
on diluted factor X before loading onto an anion exchanger for further purification;
on factor X eluted from an anion exchanger; and on virus-filtered factor X.

Preferably, the activation is carried out at some stage after the immobilised metal ion affinity chromatography step, because anything earlier might activate any other clotting factors present in the starting material and compromise their suitability for manufacture into other therapeutic products. Ideally, the activation step is carried out as late as possible in the manufacturing process, as once activated, the factor X may be more labile (i.e. less stable). Also ideally, the activation step is carried out at a stage in the method which allows the activated factor X to be stored pending analysis before final formulation, filling and freeze-drying. Most preferably, activation takes place between the anion exchange step and formulation of the virus-filtered factor X.

Activation of factor X to factor Xa can be carried out using any suitable method. For example, factor X can be activated by calcium alone, or in combination with a venom such as Russell's Viper Venom. Other metal ions, particularly divalent metal ions such as magnesium, can also potentiate the activation of factor X. To minimize any risk of activation chemicals remaining in the final product, the activator can be immobilised on a solid matrix and a factor X solution passed through the matrix. Activation occurs during the passage and the factor X flows through without dilution. For example, metal ions may be immobilised on a chelating matrix. Alternatively, activation with metal ions can be done in solution and the solution passed through a chelating matrix to remove the metal ions afterwards. Venoms such a Russell's Viper Venom can be immobilised on ligand-activated matrices such as CNBr-activated Sepharose or epoxy-activated Sepharose.

At earlier stages in the factor X purification process, it may be possible to use the feedback mechanism whereby residual prothrombin is converted to thrombin by small amounts of activated factor X and the thrombin then accelerates the activation of more factor X. Factor X may alternatively be activated by a temperature drop in the presence of factor VII thus utilising the "cold-activation" of factor VII, with the factor VII then activating factor X.

The invention also provides a pharmaceutical composition comprising factor X or factor Xa and one or more pharmaceutically acceptable diluents, excipients and/or stabilizers. Preferably, the factor X or factor Xa is factor X or Xa prepared by the method of the invention, although any factor X or factor Xa of suitable purity may be used. Factor X or factor Xa is preferably at least 30% by weight, more preferably at least 70% by weight of the total protein present in any pharmaceutical composition, and most preferably is the only protein present. The composition may be a frozen solution, in liquid form or freeze dried, but is preferably freeze dried in order to maximise the shelf life. Freeze dried compositions are also preferable as they may be subjected to a dry heat treatment step for the inactivation of viruses.

Suitable stabilizers are compounds which help stabilize the factor X or factor Xa during freeze drying and/or heat treatment steps (i.e. help maintain factor X or factor Xa activity across these steps). Depending on the clinical indication for use of the composition, such stabilizers include, but are not limited to, carbohydrates such as sucrose, trehalose and dextran; amino acids such as glycine; polyvinylpyrrolidone; and polyethylene glycols. A preferred stabilizer is sucrose.

For a factor X or factor Xa solution for infusion, a pH between about 6.0 and about 8.0 and a salt concentration between about 150 mM and about 400 mM sodium chloride would be acceptable. Suitable buffers include those with citrate and phosphate concentrations between 5 mM and 50 mM, and sodium chloride concentrations between 50 mM and 400 mM. A preferred freeze dried composition comprises, on reconstitution, 1-2% w/w sucrose and 150-300 mM sodium chloride at a pH of 6.5-7.3. A more preferred formulation comprises 1% w/w sucrose, 10 mM citrate, 10 mM phosphate and 200-300 mM sodium chloride at a pH of 7.3.

The amount of factor X in the final product should be such that, on reconstitution, it can provide a solution containing between about 20 and about 200 international units of factor X per mL (or an equivalent amount of factor Xa when required for particular clinical applications). The desired concentration will be mainly governed by clinical, pharmaceutical and commercial considerations.

The freeze dried compositions of the invention can be prepared by adding a stabilizer and any additional formulation ingredients to a solution of factor X or factor Xa. The solution may optionally be sterile filtered, for example through a 0.2 µm pore size filter, before being filled into suitable containers, for example glass vials. The containers are then freeze dried. Suitable freeze drying conditions are freezing at about -50° C.; primary drying for about 72 to 98 hours at a shelf temperature of about -20 to -34° C., preferably about -25 oC, and a chamber pressure of about 17 to 200 μ bar, preferably about 100 μ bar; and secondary drying for about 18 hours at a shelf temperature of about +28 to +32° C., preferably +30° C. and a chamber pressure of about 0 to 60 μ bar, preferably about 30 μ bar. At the end of secondary freeze-drying, the containers are closed under vacuum and oversealed.

The composition ingredients are preferably selected such that the composition is stable over prolonged storage times, preferably 2-3 years, can be stored at room temperature, and can be readily reconstituted to give a factor X or factor Xa solution suitable for clinical use. Reconstitution of a freeze dried composition may be carried out by introducing sterile water for injections into the vial by an aseptic method. In practice, this involves the transfer of sterile water into the vial using a needle and syringe or a commercial device for transferring pharmaceutical solvents. The freeze-drying process leaves the product in the vial under partial vacuum, so water is drawn into the vial by the vacuum, which can help the reconstitution process. The quicker the reconstitution the better, as the product could be needed by a patient experiencing a critical bleed. A reconstitution time of about 1-10 minutes is acceptable, but preferably the reconstitution time is less than about 60 seconds, and more preferably less than about 30 seconds.

The freeze dried factor X or factor Xa concentrate can be subjected to a dry heat
treatment virus reduction step. Suitable conditions include heating between 60° C. and 100° C. for between 1 and 144 hours. Generally, lower temperatures and/or shorter treatment times will result in higher yields of functional protein but less efficient virus inactivation. The preferred conditions are heat-treatment at about 80° C. for about 72 hours as this has been found to provide both good virus inactivation and acceptable yield of factor X.

Factor X or factor Xa prepared according to the method of the invention and the factor X or factor Xa compositions of the invention may be used for the treatment of factor X deficiency, and any other conditions for which treatment with factor X has been proposed. In particular, the method of the invention allows the preparation of highly-purified factor X or factor Xa with multiple virus inactivation steps and which can be presented to the patient in a small volume, concentrated formulation. The formulations of the invention also provide a stable freeze-dried product which can be stored for extended periods at ambient or elevated temperatures.

Factor X, including that prepared according to the method of the invention and the factor X compositions of the invention, may also be used for the treatment of patients who have developed inhibitors to blood clotting proteins. Some patients (about 5-10%) with factor VIII or factor IX deficiency (Haemophilia A or B) develop inhibitors or autoantibodies in response to replacement therapy with concentrates of factor VIII or factor IX. These patients are extremely difficult to treat during acute bleeding episodes which can be life-threatening. Factor X concentrate and/or activated factor X (factor Xa) concentrate could be used to treat these patients by stopping acute bleeding episodes.

Factor X acts directly at the penultimate stage of the blood clotting reaction process. Factor X is activated and then catalyses the activation of prothrombin to thrombin which in turn cleaves fibrinogen and factor XIII to form the cross-linked fibrin clot. Factor VIII is a cofactor in the activation of factor X which is catalyzed by activated factor IX. Thus deficiency of either factor VIII or factor IX could be by-passed by supplementation therapy with factor X or activated factor X (i.e. factor Xa). The rationale for efficacy of factor X concentrate is that by raising the plasma concentration of factor X, the reaction equilibrium would move toward the endogenous generation of factor Xa, thereby driving the clotting cascade reaction towards clot formation. The rationale for efficacy of factor Xa concentrate is that the thrombin generation from prothrombin would be driven by the natural catalyst (factor Xa) albeit by infusion rather than reliance on the earlier stages of coagulation pathway activation.

The use of factor X or factor Xa to treat patients with factor VIII or factor IX deficiency forms a further feature of the invention. Thus, the invention also provides a method of treating factor VIII or factor IX deficiency in a patient, the method comprising treating the patient with a therapeutically effective amount of factor X or factor Xa. The invention also provides factor X or factor Xa for use in treating factor VIII or factor IX deficiency in a patient.

Factor X or factor Xa, including that prepared according to the method of the invention and the factor X or factor Xa compositions of the invention, may also be used as a haemostatic aid for patients who do not have factor X deficiency but who are suffering from haemorrhage or the risk of haemorrhage. Treatment with factor X or activated factor X (factor Xa) may serve to correct the haemostatic imbalance, thus promoting coagulation.

The use of factor X or factor Xa to treat patients suffering from haemorrhage or the risk of haemorrhage forms a further feature of the invention. Thus, the invention also provides a method of treating or preventing haemorrhage in a patient, the method comprising treating the patient with a therapeutically effective amount of factor X or factor Xa. The invention also provides factor X or factor Xa for use in treating or preventing haemorrhage.

Factor X, including that prepared according to the method of the invention and the factor X compositions of the invention, may also be used for anticoagulant reversal. Some anticoagulants work by depleting the plasma of functional clotting factors. Sometimes it is necessary to reverse this effect as quickly as possible, for example to allow emergency surgery. This is currently achieved by injection of prothrombin complex concentrate (PCC) which is a mixture of clotting factors. However, as the balance of clotting factors in PCC does not match the balance in anticoagulated patients, there can be hazards associated with loss of haemostatic control when the PCC is infused. Use of factor X concentrate, possibly alongside other purified clotting factors, may provide better clotting control in a patient.

The use of factor X or factor Xa for anticoagulant reversal forms a further feature of the invention. Thus, the invention also provides a method of reversing the effect of an anticoagulant in a patient, the method comprising treating the patient with a therapeutically effective amount of factor X or factor Xa. The invention also provides factor X or factor Xa for use in anticoagulation reversal.

Inactivated factor X may be used for the treatment of patients with a thrombotic tendency. Some patients have a thrombotic tendency or hypercoagulable condition which can be treated with anticoagulants. Historically the choice of treatment has been limited to warfarin and its analogues (which inhibit the carboxylation of clot-forming Vitamin K-dependent clotting factors) or heparin and its analogues (which catalyse the inhibition of activated clotting factors by protease inhibitors). Some conditions (e.g. pregnancy or surgery) do not favour the use of these therapies, either because of concern about toxicity or because they complicate the rapid measurement and control of acute bleeding problems. Treatment with an inactivated factor X concentrate could reduce the thrombotic tendency by anticoagulant action. The advantage of treatment with a purified inactivated factor X concentrate is that there would be very little other protein present which could cause unwanted side-effects.

The rationale for this treatment is that a suitably inactivated factor X would have no catalytic capability to convert prothrombin to thrombin (due to denaturation of the factor X active site) but would retain capability to bind to the natural substrates in blood. The inactivated factor X would compete for these sites with the endogenous active factor X. If administered at an appropriate dose, the inactivated factor X could saturate the substrate sites, down-regulating the clotting system.

The use of inactivated factor X or inactivated factor Xa as an anticoagulant forms a further feature of the invention. Thus, the invention also provides a method of treating or preventing coagulation in a patient (e.g. a thrombotic or hypercoagulable state), the method comprising treating the patient with a therapeutically effective amount of inactivated factor X or inactivated factor Xa. The invention also provides inactivated factor X or inactivated factor Xa for use as an anticoagulant, and pharmaceutical compositions comprising inactivated factor X or inactivated factor Xa and one or more pharmaceutically acceptable diluents, excipients and/or stabilizers.

Inactivated factor X or inactivated factor Xa is preferably at least 30% by weight, more preferably at least 70% by weight of the total protein present in any pharmaceutical composition, and most preferably is the only protein present. The composition may be a frozen solution, in liquid form or freeze dried, but is preferably freeze dried in order to maximise the shelf life. Freeze dried compositions are also preferable as they may be subjected to a dry heat treatment step for the inactivation of viruses.

Any method of inactivation which causes denaturation of the factor X active site without destroying the capability of the factor X to bind to natural substrates in blood can be used to inactivate the factor X or factor Xa. For example, factor X (or factor Xa) can be inactivated by heat (e.g. at 60° C. in solution for >20 hours, or at 80° C. for 72 hours after lyophilisation in a formulation which renders the factor X more susceptible to inactivation, e.g. a formulation containing polyvinyl pyrrolidone, or polyethylene glycol, of low ionic strength and/or of high sugar content), by exposure to a source of gamma irradiation, or by reaction with denaturing or cross-linking chemicals. Inactivation can be verified by assaying for factor X activity before and after the treatment. Any factor X or factor Xa could be inactivated for use as an anticoagulant. Preferably, the factor X or factor Xa would be prepared according to the method of the invention or would be a factor X or factor Xa composition according to the invention. Thus, in another aspect, the methods of the invention further comprise an inactivation step to inactivate factor X or factor Xa.

Administration of factor X, factor Xa, inactivated factor X or inactivated factor Xa to a patient will normally be via intravenous administration of a suitable solution. Other routes of administration (e.g. subcutaneous, oral) may be used in the presence of a suitable carrier, but clinical response may be delayed and/or reduced and thus intravenous administration is preferred. Suitable dosage regimens will depend on the patient and condition being treated and on the mode of administration. In chronic conditions such as factor X deficiency, repeated treatments will be necessary. For other conditions, a single treatment may be sufficient.

Any and all possible combinations of preferred features disclosed herein form part of the invention, even if such combinations are not explicitly disclosed.

The following assay methods may be used to measure protein activity in the methods and compositions of the invention.

Clotting Assay for Factor X

Factor X can be measured in a clotting assay which uses factor X-deficient plasma as the substrate. Test material is added to the plasma at predetermined dilution(s) and the clotting time of the plasma after re-calcification is measured. The clotting time is then compared to the clotting times obtained from dilutions of a factor X standardised preparation (e.g. the WHO International Standard for factors II, IX and X) and the concentration of factor X is interpolated.

Chromogenic Assay for Factor X

Factor X can be measured by first activating the factor X with Russell's Viper venom factor X specific activator and then determining the increase in absorbance due to release of a chromophore from a commercial chromogenic peptide substrate (e.g. Chromogenix S2765). This is then compared to the absorbance change obtained from dilutions of a factor X standardised preparation (e.g. the WHO International Standard for factors II, IX and X) and the concentration of factor X is interpolated.

Antigenic Assay for Factor X (ELISA)

Factor X antigen can be measured by enzyme linked immunosorbant assay with antibodies specific to factor X, one of which is conjugated to a peroxidase enzyme. Addition of a peroxidase specific substrate results in the release of a chromophore. This is then compared to the absorbance change obtained from dilutions of a factor X standardised preparation (e.g. the WHO International Standard for factors II, IX and X) and the concentration of factor X is interpolated.

Chromogenic Assay for Prothrombin

Prothrombin can be measured by first activating the prothrombin with Ecarin and then determining the increase in absorbance due to release of a chromophore from a commercial chromogenic peptide substrate (e.g. Chromogenix S2238). This is then compared to the absorbance change obtained from dilutions of a prothrombin standardised preparation (e.g. the WHO International Standard for factors II, IX and X) and the concentration of prothrombin is interpolated.

Protein Assay

The Pierce BCA assay combines the well known reduction of $Cu^{2+}$ to $Cu^+$ by protein in an alkaline medium (biuret reaction) with the highly sensitive and selective colormetric detection of the $Cu^+$ using a unique reagent containing bicinchoninic acid.

The invention is further illustrated in the following non-limiting examples.

EXAMPLE 1

Separation of Prothrombin from Factor X Using Metal Chelate Chromatography

Prothrombin complex was applied to a column of chelating Sepharose which had been charged with copper ions. After washing with 50 mM citrate 50 mM phosphate 500 mM sodium chloride buffer at pH 6.5, factor X was recovered by elution with buffer containing 50 mM citrate 50 mM phosphate 100 mM sodium chloride at pH 7.0. Consecutive equal fractions were collected from the first observed rise in eluate absorbance at 280 nm until the return to baseline. Factor X and prothrombin were measured in each fraction. Results are shown in Table 1-1.

TABLE 1-1

Factor X and Prothrombin 5 elution from metal chelate chromatography

| Fraction | Factor X, iu/mL | Prothrombin, iu/mL | Prothrombin, iu per unit of factor X |
|---|---|---|---|
| 1 | 17.3 | 0.49 | 0.028 |
| 2 | 19.7 | 0.37 | 0.019 |
| 3 | 18.7 | 0.22 | 0.012 |
| 4 | 21.1 | 0.17 | 0.008 |
| 5 | 19.7 | 0.13 | 0.006 |
| 6 | 22 | 0.10 | 0.005 |
| 7 | 18.4 | 0.08 | 0.004 |
| 8 | 17.4 | 0.07 | 0.004 |
| 9 | 16.2 | 0.06 | 0.004 |
| 10 | 16 | 0.06 | 0.003 |
| 11 | 13.6 | 0.005 | 0.004 |
| 12 | 13.7 | 0.05 | 0.003 |
| 13 | 12.8 | 0.04 | 0.003 |

This Example demonstrates that whilst the factor X content of each fraction was reasonably constant, the prothrombin content fell significantly after the first few fractions.

EXAMPLE 2

Further Purification of Factor X by Anion Exchange Chromatography

Factor X-rich eluate from metal chelate chromatography was diluted to reduce ionic strength then applied to a column of DEAE-Sepharose, which had been packed and equilibrated in citrate phosphate buffer. The loaded column was washed with the same equilibration buffer and then eluted with citrate-phosphate buffer containing sodium chloride. The eluate was collected and assayed for factor X and prothrombin. The different buffer compositions are shown in Table 2-1 and results are shown in Table 2.2. These show how buffer conditions can be modified to remove prothrombin from factor X, reduction in phosphate and pH both being preferred embodiments of the invention.

TABLE 2-1

Buffer compositions used for different runs

| Run | Citrate | Phosphate | NaCl | pH |
|---|---|---|---|---|
| | Equilibration Buffer, mM | | | |
| A | 10 | 0 | 100 | 6.0 |
| B | 10 | 10 | 100 | 7.0 |
| C | 10 | 0 | 100 | 6.0 |
| D | 10 | 0 | 100 | 6.0 |
| | Elution Buffer, mM | | | |
| A | 10 | 10 | 310 | 7.0 |
| B | 10 | 10 | 310 | 7.0 |
| C | 12 | 0 | 310 | 6.5 |
| D | 10 | 10 | 310 | 7.0 |

TABLE 2.2

Separation of factor X from prothrombin using different buffer formulations

| | Eluate | | | |
|---|---|---|---|---|
| Run | Factor X, iu/mL | Prothrombin, iu/mL | Prothrombin, iu per factor X iu | Prothrombin reduction factor |
| A | 204 | 0.075 | 0.00037 | 23-fold |
| B | 673 | 2.35 | 0.0035 | 2.4-fold |
| C | 162 | 0.034 | 0.0021 | 40-fold |
| D | 259 | 0.50 | 0.0019 | 2.9-fold |

EXAMPLE 3

Improved Removal of Prothrombin by Metal Chelate Chromatography

Solvent-detergent treated prothrombin complex was applied to a column of chelating Sepharose which had been charged with copper ions. After washing with 50 mM citrate 50 mM phosphate 500 mM sodium chloride buffer pH 6.5, factor X was recovered by elution with buffer containing 50 mM citrate 50 mM phosphate 100 mM sodium chloride buffer pH 7.0. Factor X was collected either from when the eluate absorbance at 280 nm started to increase until when it had returned to baseline (Method A, as described in WO 89/05650) or for a quantity of 3.3 gel bed 15 volumes starting 1.2 gel bed volumes after the rise in eluate absorbance (Method B according to the invention). Results are shown in Table 3-1.

TABLE 3-1

Mean composition of metal chelate eluate collected by different methods

| Method | Factor X, iu/mL | Prothrombin, iu/mL | Prothrombin, iu per iu of factor X | Prothrombin removal factor |
|---|---|---|---|---|
| A (n = 7) | 15.9 | 0.42 | 0.026 | — |
| B (n + 6) | 16.8 | 0.12 | 0.007 | 3.7-fold |

EXAMPLE 4

Further Purification and Formulation of Factor X to Yield Active and Nonactive Products Factor X was prepared by purification of solvent-detergent treated prothrombin complex using the metal chelate chromatography method of the invention. The factor X was then applied to a column of DEAE Sepharose FF equilibrated in citrate buffer containing 100 mM sodium chloride at pH6.0. The factor X was eluted as a single peak using a citrate-phosphate buffer containing 310 mM sodium chloride at pH7.0.

The factor X eluate was formulated with buffer containing different potential stabilizers, dispensed into glass vials and freeze-dried. On completion of freeze-drying, the vials were sealed and then subjected to the virus-inactivation process of heating at 80° C. for 72 hours. The start material and product were then reconstituted and assayed. Reconstitution time, solution appearance and factor X yield were measured. Factor X yield is evidence of the retained protein capacity for activation (high yield) or the amount of protein inactivation/denaturation (low yield). Table 4-1 shows formulations which resulted in good reconstitution properties and yield of factor X activity. Table 4-2 shows formulations which resulted in factor X inactivation (low yield), suitable for the preparation of an inactivated factor X product.

| Formulation | Reconstitution time, seconds | Solution Appearance | Factor X yield, % |
|---|---|---|---|
| 10 mM citrate, 10 mM Phosphate, 150 mM Sodium Chloride pH 7.3 + 0.5% sucrose | <25 | Clear | 74 |
| 10 mM citrate, 10 mM Phosphate, 150 mM Sodium Chloride pH 7.3 + 1% sucrose | <20 | Clear | 88 |
| 10 mM citrate, 10 mM Phosphate, 210 mM Sodium Chloride pH 6.5 + 0.5% sucrose | <20 | Clear | 70 |
| 10 mM citrate, 10 mM Phosphate, 250 mM Sodium Chloride pH 6.8 + 2% sucrose | <20 | Clear | 78 |
| 10 mM citrate, 10 mM Phosphate, 250 mM Sodium Chloride pH 7.0 + 1% sucrose | 25 | Clear | 84 |
| 10 mM citrate, 10 mM Phosphate, 250 mM Sodium Chloride pH 7.3 + 2% sucrose | <20 | Clear | 84 |
| 10 mM citrate, 10 mM Phosphate, 300 mM Sodium Chloride pH 7.3 + 0.5% sucrose | <25 | Clear | 74 |
| 10 mM citrate, 10 mM Phosphate, 300 mM Sodium Chloride pH 7.3 + 3% sucrose | <20 | Clear | 73 |
| 10 mM citrate, 10 mM Phosphate, 400 mM Sodium Chloride pH 7.3 + 1% sucrose | <20 | Clear | 77 |
| 10 mM citrate, 10 mM Phosphate, 400 mM Sodium Chloride pH 7.3 + 1.5% sucrose | <25 | Clear | 81 |
| 10 mM citrate, 10 mM Phosphate, 300 mM Sodium Chloride pH 7.3 + 1% trehalose | <20 | Clear | 92 |
| 10 mM citrate, 10 mM Phosphate, 300 mM Sodium Chloride pH 7.3 + 3% trehalose | <20 | Clear | 82 |
| 10 mM citrate, 10 mM Phosphate, 270 mM Sodium Chloride pH 6.0 + 1% sucrose, 1% Dextran 35-45K. | <25 | Clear | 72 |
| 10 mM citrate, 10 mM Phosphate, 250 mM Sodium Chloride pH 7.0 + 20 mM glycine | <20 | Clear | 52 |

TABLE 4-2

Formulations resulting in factor X inactivation

| Formulation | Reconstitution | Solution Appearance | Factor X yeild, % |
|---|---|---|---|
| 10 mm citrate, 10 mm Phosphate, 240 mm Sodium Chloride ph 6.5 + 3% SUCROSE | 45 | Clear | 1.6 |
| 10 mM citrate, 10 mM Phosphate, 200 mM Sodium Chloride pH 6.5 + 3% SUCROSE | >300 | Clear | 0 |
| 10 mM citrate, 10 mM Phosphate, 200 mM Sodium Chloride pH 7.3 + 3% sucrose | >300 | Clear | 0.8 |
| 10 mM citrate, 10 mM Phosphate, 200 mM Sodium Chloride pH 6.8 + 3% sucrose | >300 | Clear | 0.8 |
| 110 mM citrate, 10 mM Phosphate, 250 mM Sodium Chloride pH 7.0 + 1% sorbitol | >600 | Coloured Precipitate | 0.8 |
| 10 mM citrate, 10 mM Phosphate, 250 mM Sodium Chloride pH 7.0 + 1% PVP 40K | 48 | Clear | 13 |
| 10 mM citrate, 10 mM Phosphate, 250 mM Sodium Chloride pH 7.0 + 1% PEG 4000 | >20 | Clear | 27 |

(In Table 4-2, PVP = polyvinyl pyrrolidone, and PEG = polyethylene glycol).

EXAMPLE 5

Demonstration that Inactivated Factor X Will Inhibit the Coagulation Process

Factor X prepared by the method of the invention was inactivated by heating in solution at 60° C. for >20 hours. Inactivation was verified by assaying for factor X activity before and after the treatment.

Two standard clinical laboratory coagulation tests were used to determine the effect of adding the inactivated factor X to normal pooled plasma. 50 μl of inactivated factor X was mixed with 50 μl of pooled human normal plasma. 50 μl of fully-functional factor X or factor X formulation buffer were substituted for the inactivated factor X in some tests to serve as positive and negative control respectively. As a further control, additional calcium was used in one set of tests to overcome possible calcium-chelation by citrate ions in the factor X formulation buffer. The samples were then assayed in the prothrombin time (PT) test or the activated partial thromboplastin time (APTT) test. These two tests are well established in haematology and coagulation laboratories where they are used to distinguish between clinical defects in the extrinsic or intrinsic coagulation mechanisms.

PT method: 50 μl of test sample and 50 μl of plasma were incubated for 60 seconds then 100 μl Stago Neoplastine (rabbit brain thromboplastin+Calcium chloride) was added. The clotting time was measured.

APTT method: 50 μl of test sample and 50 μl of plasma were mixed with 50 μl DAPTTIN (kaolin, sulphatide+highly purified phospholipid) and incubated for 180 seconds. 100 ul 25 mM calcium chloride was added and the clotting time was measured.

Results are shown in Tables 5-1 and 5-2.

TABLE 5-1

Prothrombin Time

| | Factor X deactivated at 100 iu/ml in formulation buffer (sec) | Factor X at 100 iu/ml in formulation buffer (sec) | Assay buffer (sec) |
|---|---|---|---|
| No sample dilution | 34.7 | 21.6 | 15.2 |
| 1:10 dilution | 16.3 | 15.5 | |
| 1:100 dilution | 13.8 | 15.0 | |
| Added 10 mM CaCl$_2$: | | | |
| No sample dilution | 32.9 | 17.6 | |
| 1:10 dilution | 16.9 | 14.5 | |
| 1:100 dilution | 14.2 | 14.6 | |

TABLE 5-2

Activated Partial Thromboplastin Time

| | Factor X deactivated at 100 iu/ml in formulation buffer (sec) | Factor X at 100 iu/ml in formulation buffer (sec) | Formulation Buffer (sec) | Assay buffer (sec) |
|---|---|---|---|---|
| No sample dilution | 70.3 | 41.2 | 37.7 | 33.0 |
| 1:10 dilution | 33.1 | 31.3 | 31.5 | |
| 1:100 dilution | 32.1 | 30.7 | 33.9 | |
| Added 10 mM CaCl$_2$: | | | | |
| No sample dilution | 60.5 | | 22.5 | |
| 1:10 dilution | 35.8 | | 31.9 | |
| 1:100 dilution | 32 | | 32.1 | |

These results show that both the prothrombin time and the activated partial thromboplastin time were prolonged by addition of the inactivated factor X in a dose-dependent manner. The effect was attributable to inactivated factor X. No effect was seen on the PT with native, active factor X and only a much smaller effect was seen on the APTT with native, active factor X. Buffers or salts had no effect in either test.

EXAMPLE 6

Further Purification of Factor X by Anion Exchange Chromatography

Factor X which had been eluted from a copper-charged, prothrombin complexloaded IMAC column was diluted to a conductivity of 15 mS/cm at pH6.0. It was applied to a pre-packed column of DEAE-Sepharose Fast Flow anion exchanger. The loaded column was then washed with gel equilibration buffer (approx 10.5 mM citrate 100 mM sodium chloride pH6.0). Buffer composition was then adjusted by washing with approximately 10 mM citrate 10 mM phosphate 150 mM sodium chloride pH6.0 before eluting the bound protein with approximately 10 mM citrate 10 mM phosphate 310 mM sodium chloride pH7.0. Fractions were collected across the protein elution peak and assayed for factors X, II and IX. Results were expressed as a percentage of the maximum activity (in iu/mL) for each protein (FIG. 1). Results showed that factor II and factor IX elution is retarded by this anion exchange step. The step may be used to separate factor X from factor II and factor IX by selective fraction collection.

EXAMPLE 7

Activation of Factor X and its Use to By-Pass Factor VIII Function

Factor X eluate produced by sequential anion exchange chromatography of cryoprecipitate-depleted plasma, chromatography on copper-charged chelating gel and further chromatography on anion exchanger was activated. Activation was achieved by incubation of the factor X-rich eluate with 25 mM calcium chloride and 0.01 u/mL of Russell's viper venom-X at pH7.4 at 37° C. Activated factor X was measured using a chromogenic substrate assay for factor X without the addition of assay activator. Activity was determined by interpolation from a standard calibration line generated with a standard for factor X and the normal assay activator.

The activated factor X was tested in a kaolin-activated partial thromboplastin time assay using factor VIII-deficient plasma as the substrate (50 µl factor VIIIdeficient plasma+50 µl assay buffer+50 µl dapttin TC reagent incubated at 37° C. for 180 seconds before addition of 100 µl of the test sample). The clotting times were measured and compared with those for control samples which contained only the factor X activators or non-activated factor X. Results shown in Table 7-1 demonstrate that (a) factor X can be activated by calcium chloride or by a combination of calcium chloride and RVV-X; (b) the activated factor X substantially shortens the clotting time and this shortening is greater than achieved by any of the equivalent factor X activators alone.

TABLE 7-1

Use of activated factor X as a Factor VIII by-pass

| Clotting Initiator (components reacted together for 30 minutes at 37° C. before addition to APTT substrate) | Mean FVIII-deficient APTT clotting time (seconds) |
|---|---|
| 25 mM calcium chloride | 107.0 |
| 10 iu/ml factor X + 25 mM calcium chloride + 0.01 u/ml RVV-X | 6.7 |
| 10 iu/ml factor X + 25 mM calcium chloride | 60.7 |
| 25 mM calcium chloride + 0.01 u/ml RVV-X | 23.7 |

EXAMPLE 8

Preparation of Factor X

Solvent/detergent-treated prothrombin complex concentrate was applied to a column of copper-charged Chelating Sepharose Fast Flow in a solution containing 0.5M sodium chloride. The column was washed with citrate phosphate buffer pH6.5 containing 0.5M sodium chloride. The factor X protein was then eluted with citrate phosphate buffer pH7.0 containing 0.1M sodium chloride. The protein eluted in the first 1.2 gel bed volumes was discarded. The factor X protein eluted in the next 3.3 gel bed volumes was collected. The conductivity of this factor X solution was reduced to 10-18 mS/cm and the pH reduced to 6.0, then the solution was applied to a column of DEAE Sepharose Fast Flow anion exchange gel. The column was then washed with citrate buffer containing 0.1M sodium chloride, then with citrate phosphate buffer containing 0.15M sodium chloride. Purified factor X was then eluted with citrate phosphate buffer pH7 containing 0.31M sodium chloride. The factor X was passed through a Planova 15 nm virus-retentive filter, formulated with 1% w/w sucrose, diluted to a target potency of 130 iu factor X per mL and freeze-dried. The freeze-dried factor X vials were sealed under vacuum, then heated at 80° C. for 72 hours in a hot-air oven. Results are shown in Table 8.

TABLE 8

Purification of factor X

| | Factor X, iu/mL | Factor II, in per 100 iuFX | Specific activity, iu/mg of protein | Stage Yield, % |
|---|---|---|---|---|
| S/D PCC | 41.9 | 110 | 3.5 | 100 |
| Metal chelate eluate | 12.7 | 0.88 | 109 | 24 |
| Ion-exchange eluate | 251 | 0.42 | 135 | 94 |
| Virus filtrate | 227 | 0.47 | 130 | 99 |
| Freeze dried factor X | 130 | 0.51 | 131 | 87 |
| Heat-treated factor X | 122 | 0.50 | 115 | 94 |

EXAMPLE 9

Preparation of Activated Factor X

Factor X was prepared as described in Example 8 above and diluted to approximately 10 iu/ml. The solution was then mixed with Sepharose gel to which had been coupled the factor X activating protein of Russell's Viper Venom (RVVX). Activation occurred as the factor X was incubated with the RVV-X Sepharose for up to 3 hours and the activated factor X solution was then separated from the RVV-X Sepharose. Activation was demonstrated by the appearance of the factor Xa band on SDS-PAGE run under reducing conditions. Activity was measured using a factor X assay in which the normal activator had been omitted and replaced with assay buffer. One unit of activated factor X (FXa) was defined as the activity after full activation of one international unit of factor X. The presence of native, nonactivated factor X was measured by performing the routine factor X assay containing activator. Results (shown in Table 9) confirmed that more than 90% of the maximum activation was achieved.

TABLE 9

| Test Sample | Factor X activity without assay activator, iu/mL | Factor X activity with assay activator, iu/mL |
|---|---|---|
| Factor X start material | Not measured | 9.2 |
| Factor X gel supernatant | 5.9 | 6.3 |

EXAMPLE 10

Use of Activated Factor X to By-Pass Factor VIII Clotting Function

Activated factor X was prepared as described in Example 9 above. Different concentrations were added to a modified APTT assay system in which the normal plasma substrate had been replaced with factor VIII-deficient plasma. Results are shown in Table 10. Addition of buffer or inactivated factor X (prepared as described in Example 11) failed to correct the prolonged clotting times. Addition of activated factor X achieved normal clotting parameters when added at a concentration of between 0.02 and 0.05 u/mL.

TABLE 10

Clotting times in factor VIII-deficient substrate plasma

| Sample | Clotting Time, seconds |
|---|---|
| Reference plasma | 47.4 |
| Buffer | 121.8 |
| Inactivated factor X, 20 u/mL* | 105.5 |
| 5 mM Calcium chloride | 121.8 |
| Activated factor X: | |
| 0.0005 u/uL | 108.2 |
| 0.001 u/mL | 107.7 |
| 0.025 u/mL | 94.2 |
| 0.005 u/mL | 86.9 |
| 0.01 u/mL | 72.0 |
| 0.02 u/mL | 59.2 |
| 0.05 u/mL | 39.7 |
| 0.1 u/mL | 26 |

*the amount of inactive factor X obtained from 20 iu/mL of factor X

EXAMPLE 11

Preparation of Inactivated Factor X

Factor X was prepared by purification of solvent/detergent-treated prothrombin complex concentrate by copper-charged metal chelate chelate chromatography followed by ion-exchange chromatography as described in preceding examples. Factor X at 100 iu/mL and 10 iu/mL was then inactivated by incubation at 60° C. for up to 20 hours. The inactivation of factor X was measured by clotting time assay (Table 11). A clotting time of 40 seconds approximates to 0.07 iu factor X/mL. These results show that much less than 0.07 iu/mL of activity remained after 21 hours. Thus, substantially more than 99.9% inactivation was achieved.

TABLE 11

Clotting times (seconds) for Factor X activity during inactivation process

| Factor X starting Concentration | Heating Time, hours | | | | |
|---|---|---|---|---|---|
| | 0 h | 0.5 | 2 h | 4 h | 21 h |
| 100 iu/mL | 25.9 | 32.7 | 60 | 89.8 | |
| 10 iu/mL | 31.0 | 32.1 | 35.3 | 50.8 | >150 |

EXAMPLE 12

Use of Inactivated Factor X to Inhibit Coagulation

Inactivated factor X (FX-IN) was prepared by heating factor X product at 60° C. for 20 hours. Activated factor X (FXa) was diluted and mixed with different concentrations of inactivated factor X, before adding to substrate in the Thrombin Generation Assay (TGA). Results are shown in Table 12. This shows that the coagulant effect of 0.05 u/ml FXa can be negated by the presence of between 5 and 10 units of inactivated factor X, equivalent to approximately 10-20 fold excess of inactive factor X over activated factor X.

TABLE 12

Inhibition of coagulation by inactivated factor X

| Sample | Mean lag time (minutes) | Area under curve | Velocity index |
|---|---|---|---|
| Buffer | 17.0 | 2051 | 1.6 |
| FXa, 0.1 u/mL[1] | 9.0 | 3535 | 7.6 |
| FXa, 0.05 u/mL[1] + FX-IN 0.5 u/mL[2] | 12.5 | 3290 | 5.1 |
| FX-IN 2.5 u/mL[2] | 14.0 | 3016 | 6.2 |
| FX-IN 5.0 u/mL[2] | 13.5 | 2884 | 5.6 |
| FX-IN 010 u/mL[2] | 23.0 | 1544 | 1.4 |
| FX-IN 25 u/mL[2] | 22.5 | 599 | 0.7 |
| FX-IN 50 u/mL[2] | 54.5 | 186 | 0.3 |

[1] 1 unit of FXa is defined as the amount obtained from 1 international unit of factor X after full activation.
[2] 1 unit of inactive factor X is defined as the amount obtained from 1 international unit of functional factor X

EXAMPLE 13

Absence of Thrombogenicity in Factor X Preparation

Factor X was prepared as described in Example 8. The product was tested using an in vivo rabbit stasis thrombogenicity model. The effect of Factor X at three doses (100, 200 and 400 iu/kg body weight) was compared with the effect of a physiological saline negative control. A thrombin positive control (50 iu/kg body weight) was included to demonstrate that the test system could detect a thrombogenic challenge. Products were infused into a marginal ear vein and allowed to enter the circulation for 30 seconds. A section of jugular vein was then isolated by ligature and the amount of thrombin formation was evaluated 15 minutes later. Results showed no statistical difference between the rabbits receiving factor X doses and rabbits receiving the saline negative control.

The invention claimed is:

1. A method of reversing the effect of an anticoagulant in a patient, the method comprising treating the patient with a composition comprising a therapeutically effective amount of factor X or factor Xa and one or more compounds selected from the group consisting of pharmaceutically acceptable diluents, excipients, and stabilizers, treating the patient with a composition comprising a therapeutically effective amount of factor X or factor Xa further comprising preparing the factor X or factor Xa by a process comprising
    a) adsorbing a starting material comprising factor X and prothrombin onto an immobilised metal ion affinity chromatography substrate;
    b) eluting selected adsorbed proteins from the substrate;
    c) monitoring the eluate for commencement of elution of prothrombin and factor X, discarding a first portion of the eluate and collecting a subsequent second portion of the eluate enriched in factor X; and
    d) reducing the level of residual prothrombin in the factor X obtained in step c) by anion exchange chromatography.

2. A method according to claim 1, the process further comprising
    (i) solvent detergent treatment of a starting material comprising factor X and prothrombin;
    ii) adsorbing the solvent detergent treated starting material onto an immobilised metal ion affinity chromatography substrate;
    iii) eluting adsorbed proteins from the substrate;
    iv) monitoring the eluate for commencement of elution of prothrombin/factor X, discarding a first portion of the eluate and collecting a subsequent second portion of the eluate enriched in factor X;
    v) carrying out anion exchange chromatography to reduce the level of residual prothrombin in the second portion of the eluate;
    vi) filtering the product of step v) through a virus-retentive filter;
    vii) freeze drying the filtered product of step vi), optionally in the presence of one or more stabilizers; and
    viii) subjecting the freeze dried product to a virus reduction/inactivation heat treatment step.

3. A method according to claim 1, the process further comprising an activation step to activate the factor X.

4. A method according to claim 3, the factor X being activated by a divalent metal ion alone or in combination with a venom.

* * * * *